(12) United States Patent
Melnyk et al.

(10) Patent No.: US 6,325,623 B1
(45) Date of Patent: Dec. 4, 2001

(54) DENTAL LIGHT CURING AND DIAGNOSING DEVICE

(76) Inventors: Ivan Melnyk, 604 Cottonwood Ave, Coquitlam BC (CA), V3J 2S4; Andrew H. Rawicz, 7216 Hewitt Str., Burnaby BC (CA), V5A 3M2; Pawel Kowalski, 459 Ailsa Ave., Port Moody BC (CA), V3H 1A2

(*) Notice: Subject to any disclaimer, the term of this patent is extended or adjusted under 35 U.S.C. 154(b) by 0 days.

(21) Appl. No.: 09/540,556

(22) Filed: Mar. 31, 2000

(51) Int. Cl.⁷ ..................................... A61C 1/00
(52) U.S. Cl. ............................................ 433/29
(58) Field of Search ................. 433/29, 141, 215; 385/43, 902

(56) References Cited

U.S. PATENT DOCUMENTS

| | | | |
|---|---|---|---|
| 4,666,406 | * 5/1987 | Kanca, III | 433/215 |
| 5,759,032 | * 6/1998 | Bartel | 433/29 |
| 5,791,898 | * 8/1998 | Maissami | 433/29 |
| 5,800,163 | * 9/1998 | Rueggeberg et al. | 433/29 |
| 5,975,895 | * 11/1999 | Sullivan | 433/29 |
| 6,208,788 | * 3/2001 | Nosov | 433/29 |

* cited by examiner

Primary Examiner—Todd E. Manahan

(57) ABSTRACT

A dental light curing device with an expanded functionality for diagnosing abnormalities by observation of native or induced fluorescence in the oral cavity. An optical assembly consisting of a short pass or band pass filter and a spacer is applied to the output distal end of the dental light curing device. A long pass filter is applied to the attenuating filter or the spacer is made as a long pass filter. The diagnosing sites can be seen through the spacer.

11 Claims, 6 Drawing Sheets

DENTAL LIGHT CURING AND DIAGNOSING DEVICE

BACKGROUND OF THE INVENTION

1. Field of the Invention

The invention relates generally to a dental light curing device, and more particular, to a multi-functional dental light curing device that can be used for curing and detecting oral abnormalities by viewing fluorescence emissions from oral disease sites to assist in the diagnosis of the site.

2. State of the Art

The light curing technique has been used in dentistry for many years. In fact, every dental office has at least one dental light curing device because light cured composite fillings are considered the best in the dental industry. A number of different designs of dental light curing devices have been proposed. A typical dental light curing device comprises a hand-held device which includes an enclosure with a light source, focusing optics, delivery optics and an attenuation filter. The light source is typically a halogen or metal halide lamp with a power from 30 to 100 watts. The focusing optics concentrate the lamp emission on the delivery optics which is typically a fiber optic bundle or a glass rod. The dental composite materials are cured under the blue-green light (wavelengths from 400 up to 520 nm, maximum close to 460 nm). For this reason, the focusing and delivery optics can cut the red and infrared emission that is generated by the polychromatic light sources mentioned above and can overheat the tooth. Instead of a lamp, powerful light emitting diodes can be used. The minimum light intensity required at the distal output end of the delivery optics is 200 mW/cm$^2$; however, the desirable light intensity is twice as high, about 400 mW/cm$^2$. The delivery optics is applied to the tooth by its distal output end and illuminates the tooth until the composite filling is cured (typically about one minute). Due to the high intensity of the light delivered to the tooth and high light scattering in the tooth, strongly reflected and scattered back light is suppressed an the attenuation filter. This suppression is provided in order not to overexpose the dentist's eyes to the blue-green light. The attenuation filter is located around the delivery optics. Typically, it is made of orange-red plastics that intensively absorbs the blue-green light while still making the contact zone viewable for the dentist.

Therefore, the prior art uses the powerful light from the dental curing device for strengthening dental materials only. It is useful to expand the functionality of the dental light curing device by adding the possibility to detect neoplastic abnormalities in a patient's oral cavity during the regular observation by the dentist. Such abnormalities include dysplastic or malignant lesions that are typically undetectable with white light illumination, particularly in their early stages. Dentists are instructed to perform a regular visual examination of patient's oral cavity. During such examination, the dentist examines the patient's gingiva, tongue, buccal mucosa, floor, palate, and labial mucosa paying attention to signs such as leukoplakia (white lesions) or erythropakia (red lesions) that could be precursors to cancer. Unfortunately, often such precursors became visible in the later stages of cancer when a radical means is required (surgery, chemo-or-radiotherapy) or the disease is already noncurable. It has been proven that early detection of neoplastic changes may have the greatest potential for improving a patient's quality of life and survival rates.

A fluorescence technique is able to detect neoplastic lesions in epithelial tissue in the very early stages. The prior art proposed for fluorescence tissue differentiation used special powerful light sources, such as lasers, high pressure mercury lamps, xenon lamps, etc. It often requires special conditions (cooling, ventilation) and space, is expensive, and thus, is not suitable for a regular dental office. Another prior art is based on selective accumulation of certain dyes in the neoplastic lesions, such as toluidine blue. The dye is applied to the tissue by rinsing the oral cavity. However, this prior art is still not used in dental practice because the visibility of the stained thin lesions in the oral cavity is very low, particularly, when early small lesions must be diagnosed. At the same time, toluidine blue has an intensive fluorescence emission in the red range of the visible spectrum. Also, a variety of photosensitizers have been developed to enhance the contrast between the fluorescence of abnormal and normal tissue. The tissue is sensitized by injection of the photosensitizer or by its topical application. However, this prior art also requires special light sources with maximum light intensity at the absorption band of the photosensitizer and a specific imaging technique. This requirement prevents use of such prior art in dental practice mainly due to the price.

The present invention aims to overcome the difficulties with detecting the oral abnormalities mentioned above by expanding the functionality of the existing dental technique.

SUMMARY OF THE INVENTION

It is, therefore, an object of the invention to expand the functionality of the existing dental light curing devices by adding the possibility to detect neoplastic lesions in oral cavity by fluorescence means.

It is another object of the invention to provide the detection of neoplastic lesions in oral cavity by a dental light curing device and fluorescent dyes applyed to the oral cavity.

It is also an object of the invention to provide better viewing conditions while observing the oral cavity with the dental light curing device.

The foregoing objects of the invention are achieved by adding an optical assembly to the distal output tip of the dental light curing device. The assembly provides filtration of the output light at the desirable spectral range. Preferably, this range is from 400 to 480 nm if an autofluorescence (native fluorescence) is used. If any fluorescent dye or photosensitizer is applied (stimulated or induced fluorescence), the filtered range corresponds to the long wavelength maximum absorption of the dye. The optical assembly is applied to the surface of the oral cavity (mucosa, tongue, gingiva). The fluorescence light from the tissue is observed by the dentist through a long pass filter. Preferably, this filter is applied to the existing attenuation filter that suppresses short wavelength light. The filter blocks all light having wavelengths shorter than 520 nm, in case of native fluorescence, and shorter than a specific wavelength that corresponds to a maximum fluorescence emission for fluorescence stimulated with a dye. Preferably, the fluorescent dyes are toluidine blue (maximum absorption around 620 nm, fluorescence from 640 nm), dihematoporhyrin ether or Photofrin (maximum absorption around 630 nm, fluorescence from 640 nm), 5-aminolevulenic acid (the same wavelengths as for Photofrin), hypericin (maximum absorption around 590 nm, fluorescence from 610 nm), fluorescein (maximum absorption around 450 nm, fluorescence from 520 nm).

The tissue emits fluorescence due to endogenous fluorophores existing there. The amount of these fluorophores is different for normal tissue and a neoplastic lesion (dysplasia or malignant lesion). This provides a difference in the fluorescence spectra; typically the fluorescence spectrum from a neoplastic lesion has a shift in the red region (lesion looks reddish in comparison to the light orange background) or it is substantially suppressed (lesion looks darkish under fluorescence even if it is not recognizable under white illumination). The contrast in the fluorescence can be enhanced by applying fluorescent markers or dyes that are able to accumulate in abnormal cells while almost completely releasing from normal ones. Some dyes (such as hypericin, for example) provide so high a fluorescence emission that it can be seen even with a quite bright ambient light.

The illustrations and description below provide more details explaining the present invention.

BRIEF DESCRIPTION OF THE DRAWINGS

Aspects of the present invention are illustrated, merely by way of example, in the accompanying drawings in which.

DETAILED DESCRIPTION OF THE INVENTION

Figure 1:
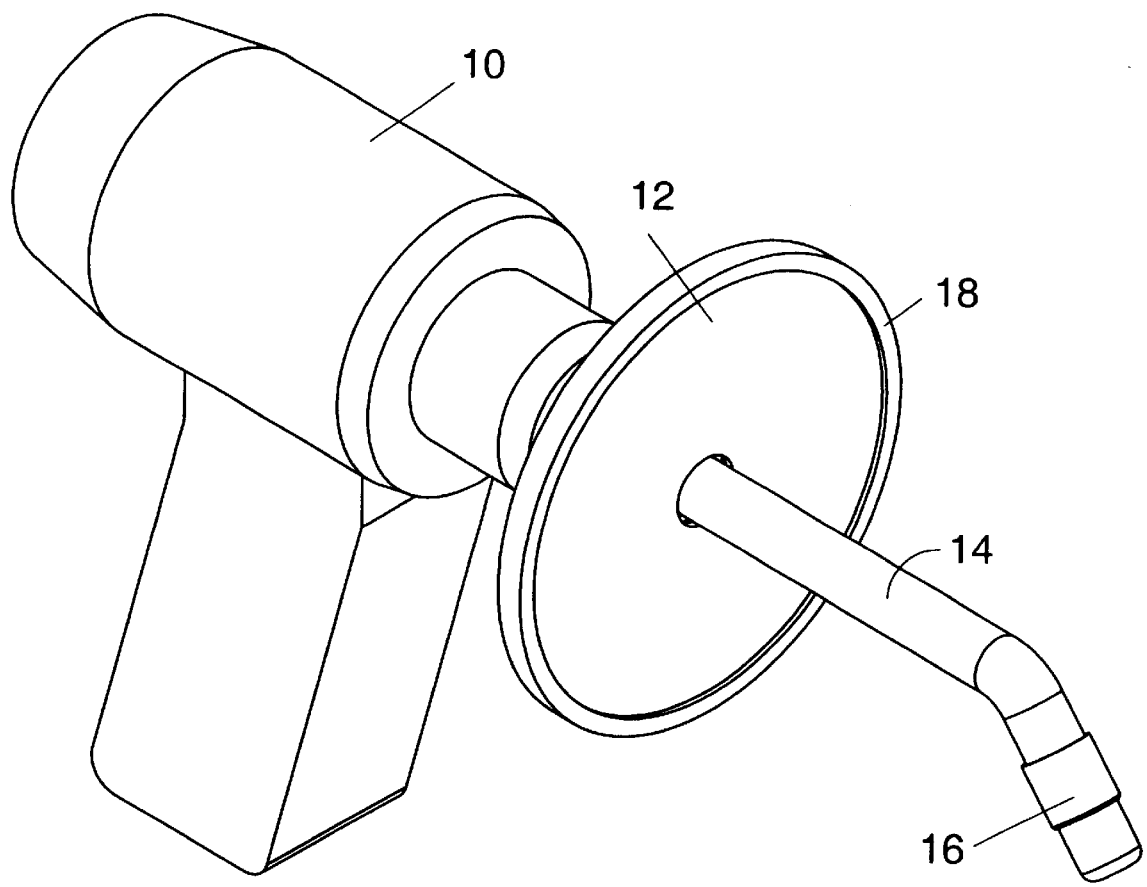
FIG. 1 is a general view of the dental light curing and diagnosing device of the present invention.
Figure 2:
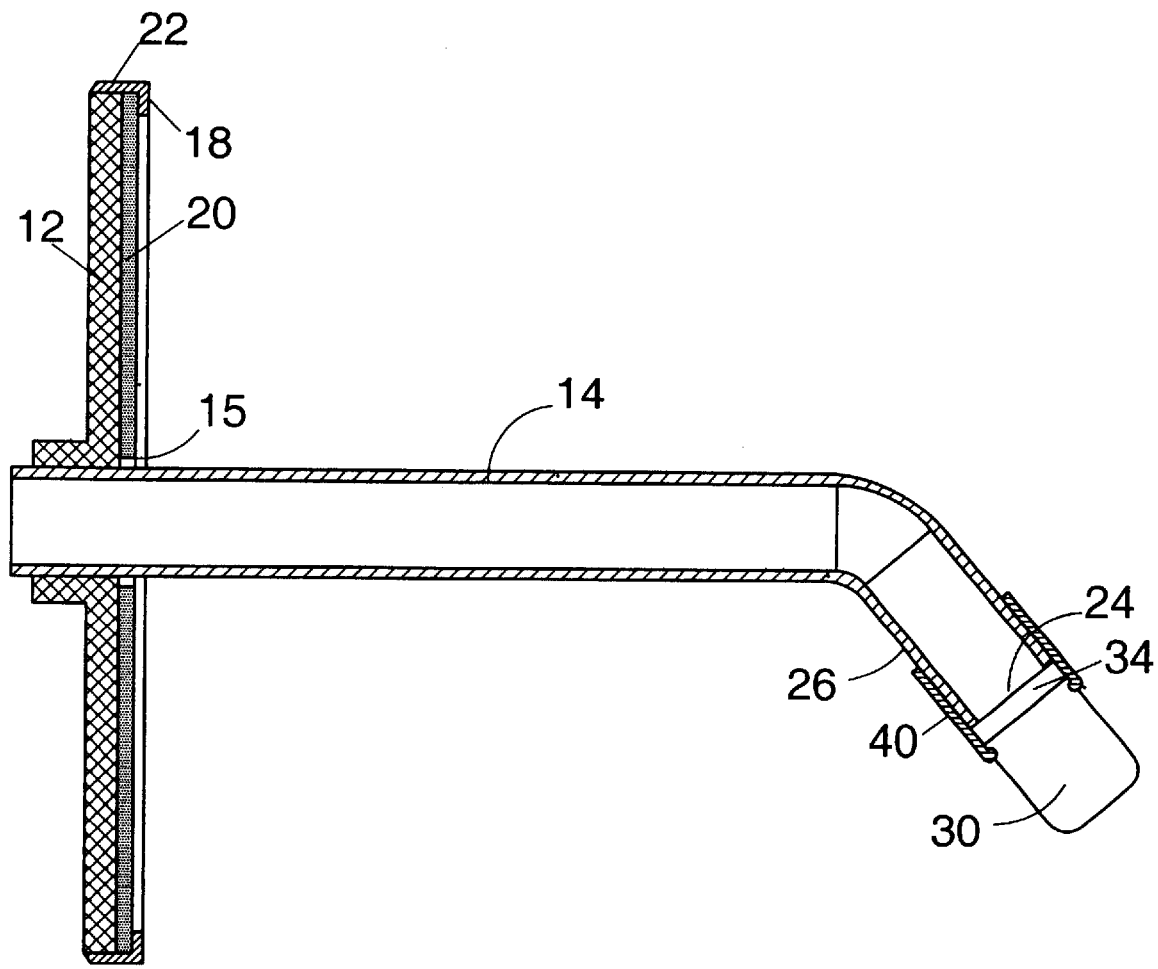
FIG. 2 is a detailed view of the delivery optics and filters of the dental light curing and diagnosing device of FIG. 1.

Referring to FIG. 1, a preferred embodiment of the dental light curing and diagnosing device is disclosed. The device comprises a conventional hand-held dental light curing apparatus (10) with an attenuation orange filter (12) and delivery optics (14). An optical assembly (16) is applied to the distal output tip of the delivery optics. An additional filter (20) mounted in a frame (18) is attached to the orange filter by a mechanical means, such as clamps (22), as shown in FIG. 2. The optical assembly (16) includes a short pass filter (34) attached to the distal tip (24) of the delivery optics (14) and a transparent spacer (30) that is attached to the short-pass filter. The short-pass filter and spacer are hold together by a flexible tubing (40) that is snapped on the output end (26) of the delivery optics. Preferably, the short pass filter is made of a colored glass filter (Schott glass BG 40, for example) and a thin metal film deposited in vacuum on top of glass. The thickness of the film and its material will determine the cutoff wavelength beyond which no light will pass through the filter. Typically, this cutoff wavelength will be in the range from 420 to 480 nm for non-stimulated (native) fluorescence and from 600 to 650 nm if some dye is applied for fluorescence enhancing. The additional filter (20) is a long pass filter, such as Schott glass OG515 or OG530 that does not transmit any light with a wavelength shorter than 515 or 530 nm, respectively. It can be also a long pass filter such as Schott glass RG630, RG645 or RG665 with corresponding cutoff wavelengths of 630, 645 and 665 nm if a fluorescent dye is used. The additional filter has an aperture (15) in its center, the diameter of the aperture is bigger than the diameter of the delivery optics. Also, it is firmly connected to the frame (18) in its peripheral part. The frame has its shape matched to the attenuation orange filter (12), such as round or elliptical. Thus, the additional filter can be easy inserted through the delivery optics and attached to the existing orange filter (12).

Figure 3:
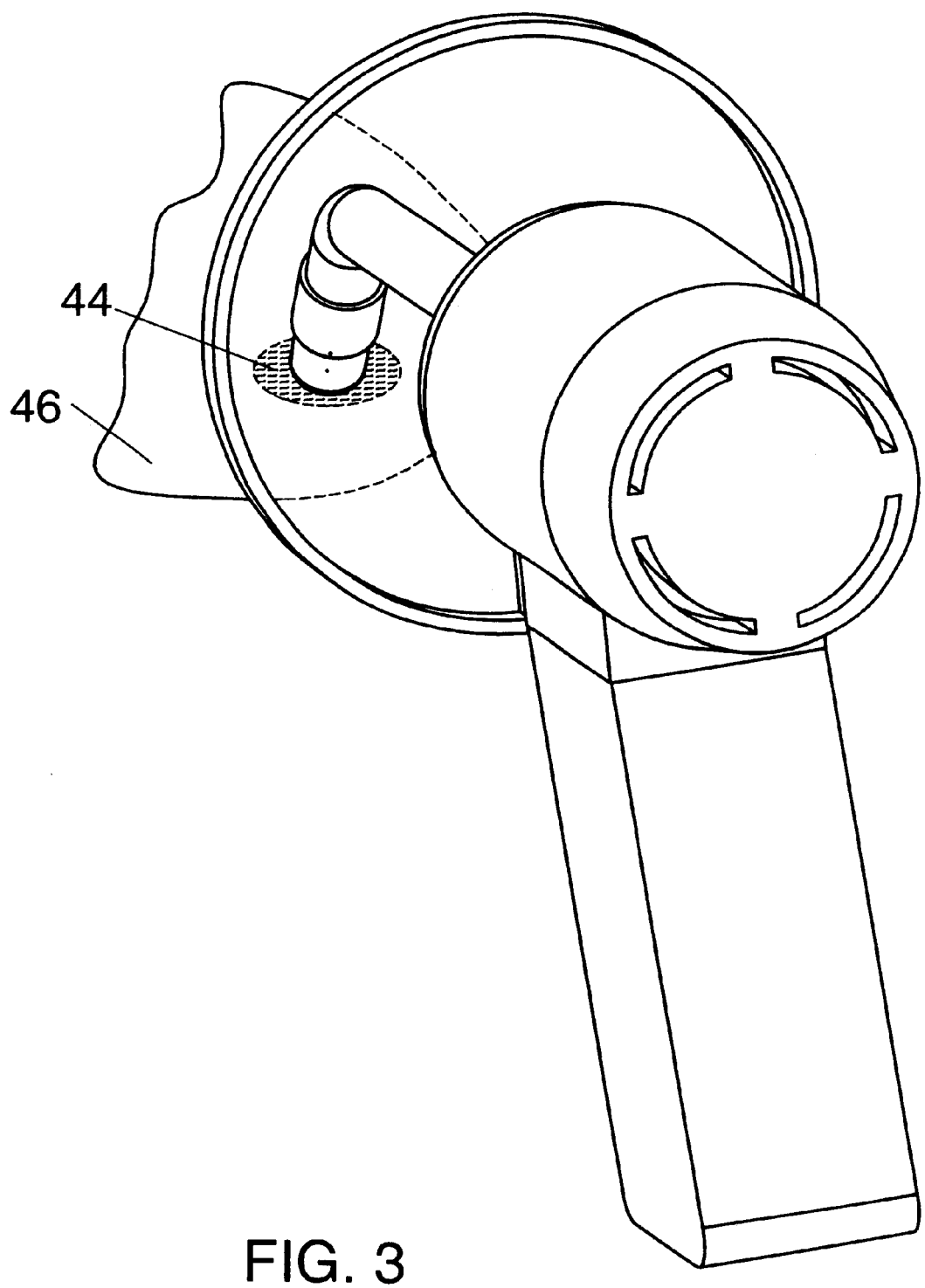
FIG. 3 is a view of the dental light curing and diagnosing device of FIG. 1 applied to the suspicious site as seen by a dentist.
Figures 4A, 4B:
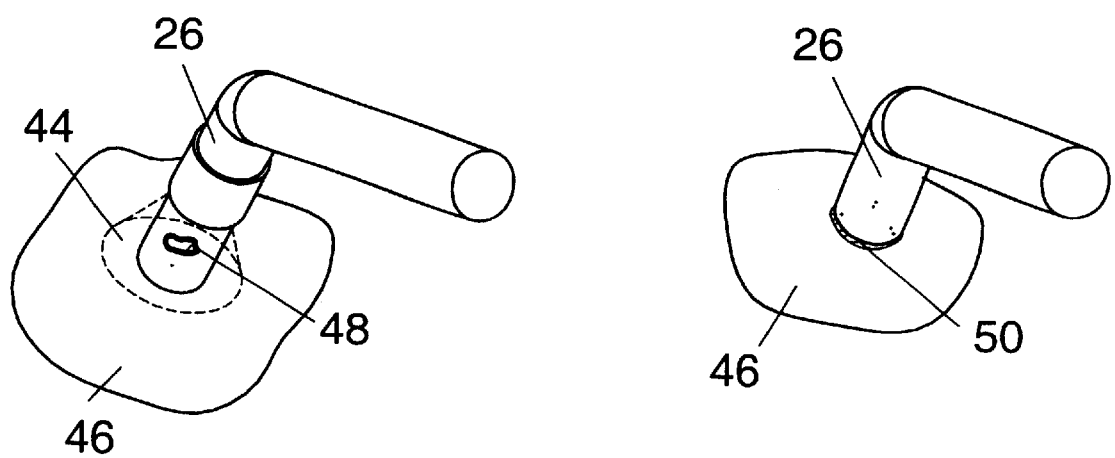
FIG. 4A is a schematic view of the illuminated area and a neoplastic lesion that is seen through the spacer of the dental light curing and diagnosing device of the present invention.
FIG. 4B is a schematic view of the illuminated area if no spacer is used.

In action, the dentist takes the enclosure (10) assembled with the filter (12) and delivery optics (14), puts delivery optics through the filter (20) with frame (18) and snaps the frame to the filter (12). Then, the dentist attaches the optical assembly (16) to the output tip of the delivery optics by snapping the tubing (40) on the distal tubular part (26). After turning on the light source (not shown) in the enclosure, the dentist applies the transparent spacer (30) to the suspicious sites in the patient's oral cavity. The dentist looks at the illuminated area (44) of the oral cavity tissue (46) through the combination of filters (12) and (20) in the same way as provided during the regular dental curing procedure, as shown in FIG. 3. The dentist can scan the surface of the tissue (mucosa, gingiva, tongue) by changing the position of the spacer (30) in the oral cavity. A neoplastis lesion will appear as a colored occlusion (48) in the illuminated area that can be seen through the spacer as shown in FIG. 4A. Its appearance will depend on the type of the lesion, typically dark or reddish on the light orange background. The observation is best provided under low ambient light conditions so as to minimize interference with the relatively weak fluorescence light. If a dye was applied, the fluorescence picture of the neoplasic lesion will be much brighter with the color corresponding to the maximum fluorescence emission of the dye.

The use of the transparent spacer (30) has a few advantages. First, it fixes the position of the output tip (26) against the tissue, and thus, provides its steady illumination which is important for fluorescence analysis. Second, it allows it to illuminate a much larger area of the tissue because the light diverges from the distal output tip. Third, the illuminated area can be viewed at full size without screening by the metallic output tip (26). If the output tip (26) is in direct contact with tissue as shown in FIG. 4B, the illuminated area represents only a narrow ring (50) around the tip (26). The ring comes from the light scattered in the tissue; the light intensity within the ring is low due to high light absorption in the tissue.

Figure 5:
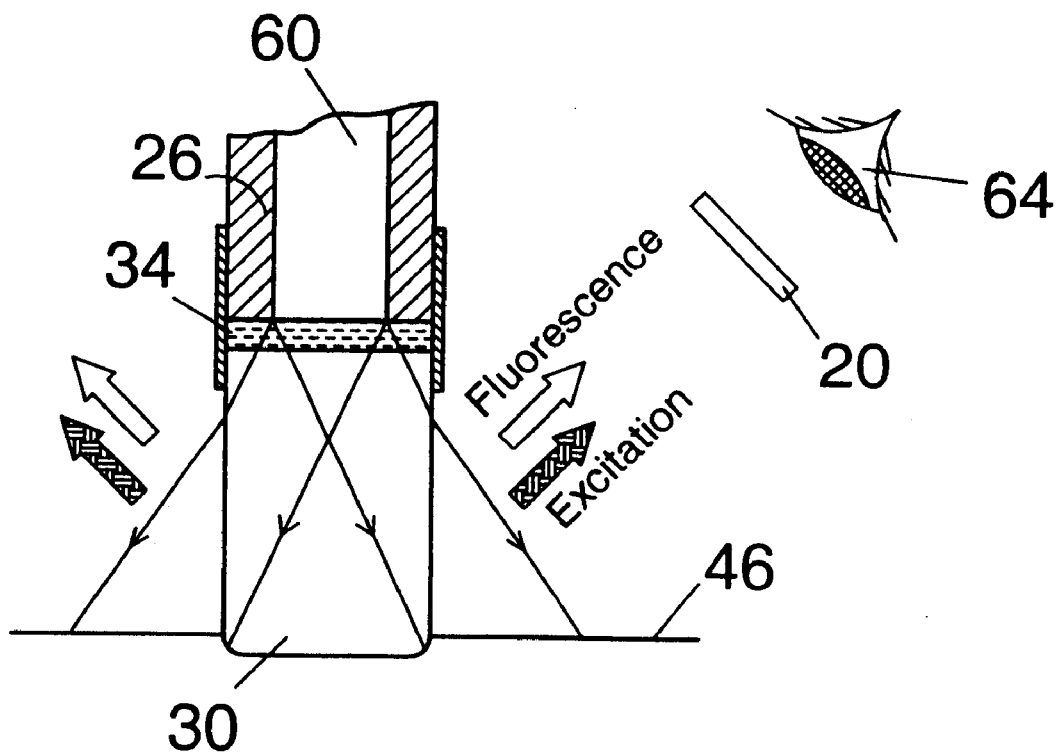
FIG. 5 is a sectional view of the transparent spacer of the dental light curing and diagnosing device of the present invention with a schematic view of the light coming from the delivery optics.

Various designs of the optical assembly (16) could be utilized in practice. As shown in FIG. 5, the spacer (30) can be made as a transparent glass rod attached to the cutoff filter (34) that is attached to the distal output tip (26) of the delivery optics. A fiber bundle (60) delivers diverged light through the filter (34), and thus, illuminates a larger area of the tissue (46) than that of an output delivery optics aperture. Incoming blue light absorbs and scatters in the tissue and excites the fluorescence light in it. The scattered excitation and fluorescence light can be seen coming through the glass rod from the illuminated area. The excitation light is blocked by the long pass filter (20) so only fluorescent light can reach the observer's eyes (64). In another embodiment, the spacer (30) is made with a central aperture (32) as shown in FIG.

6. This spacer can be cut of a tubing made of a long pass filter glass such as Schott glass OG515 or another mentioned above. An additional thin metal layer can be deposited on the outside surface of the pipe for completely excluding the short wavelength excitation light. Therefore, only fluorescent light can leave the spacer and be seen by the observer. The length of the rod can be from 5 to 20 mm, preferably from 10 to 15 mm. Preferably, its diameter is close to the diameter of the delivery optics (typically from 5 to 12 mm); thus, a simple elastic tubing can be used for fixing the spacer to the distal tip of the device.

Figure 7:
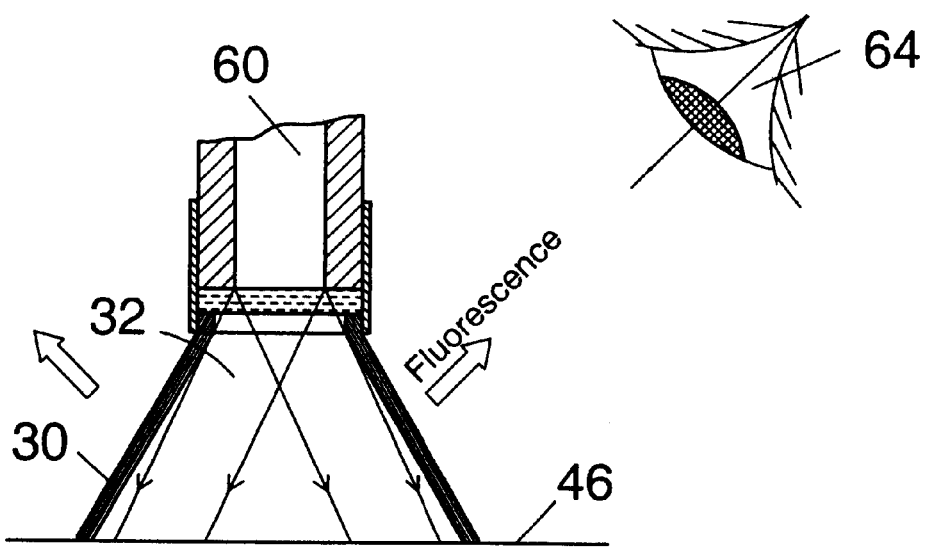
FIG. 7 is a sectional view of the spacer with a conical central aperture. The spacer is made as a long pass filter, and an angle of the cone is close to the aperture of the delivery optics.

In order to illuminate and excite a larger area, the spacer could have a conical shape with an enlarged opening facing the tissue as shown in FIG. 7. If the interior surface slopes from the spacer's axis at an angle that exceeds the angular aperture of the delivery optics, the excitation light would not be absorbed by the internal surface of the spacer, and more light will reach the tissue. The typical angular aperture of the delivery optics is from 15 to 30 degrees. Also, the conical design provides better viewing conditions for the observer because of the larger viewing angle.

Figure 6:
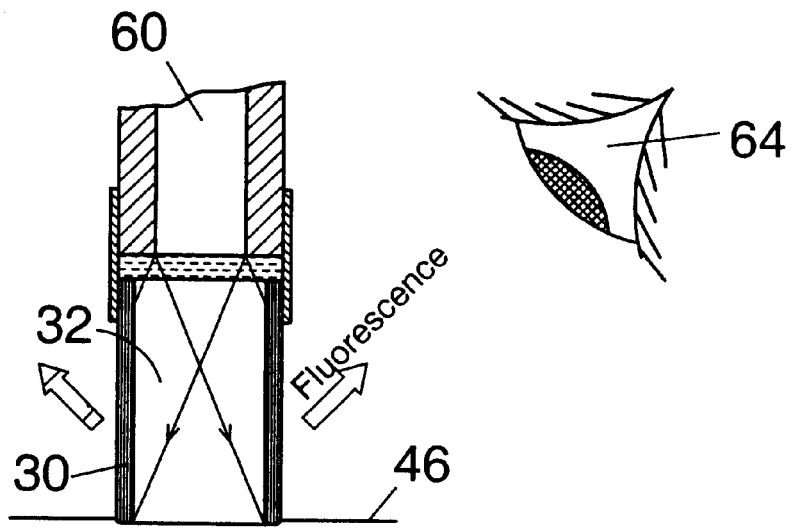
FIG. 6 is a sectional view of the spacer with a round central aperture. The spacer is made as a long pass filter.

If the spaceris made of a long pass glass filter as shown in FIG. 6 and FIG. 7, no additional filter (20) is required. In the optical assembly designs mentioned above the, spacer could be permanently connected to the short pass filter (34) by any means such as optical glue, for example. The elastic tubing (40) can be made of plastics, and it could be permanently mounted with the short pass filter and the spacer. The internal diameter of the tubing is mated with the outer diameter of the distal tip (26), and thus, provides conditions for sliding the tubing on the distal tip. The optical assembly can be separately sterilized, if necessary.

The present invention provides a number of important technical advantages that can be summarized as follows:

1. The device of the present invention provides new information for oral cavity diagnosis as compared to conventional observation by a dentist under white light illumination.

2. In comparison to known diagnostic means based on fluorescent light detection, no specific light sources are required.

3. The device of the present invention can work both with native fluorescence or fluorescence induced by any known photosensitizers.

4. The device of the present invention is inexpensive and easy to use; the additional optical components required can be easy installed, removed and sterilized, if necessary.

5. The device of the present invention provides a new, non-invasive system for performing more accurate oral cancer diagnosis.

Although the present invention has been described in some detail by way of example for purposes of clarity and understanding, it will be apparent that certain changes and modifications may be practiced within the scope of the appended claims.

What is claimed is:

1. A hand-held device for curing dental composites and diagnosing diseases of the oral cavity, comprising:

an enclosure with a light source and delivery optics producing the light necessary for curing dental composites and an attenuation filter placed around said delivery optics;

a removable optical assembly attached to the distal output end of said delivery optics, wherein said optical assembly comprises a short pass filter, a spacer attached to said filter and applied to the oral cavity surface, and a connection means that fixes said filter with said spacer and said distal output end;

said spacer can transmit light;

a removable long pass filter attached to said attenuation filter.

2. The device as claimed in claim 1 in which said spacer is made of a solid transparent glass and is from 5 to 20 mm long.

3. The device as claimed in claim 1 in which said short pass filter blocks light having a wavelength more than 470 nm and said long pass filter transmits light having a wavelength of about 520 nm and more.

4. The device as claimed in claim 1 in which said short pass filter is a band pass filter and blocks all light except that corresponds to maximum absorption of the photosensitizer applied in the oral cavity; said long pass filter transmits light having a wavelength of about 600 nm and more.

5. A hand-held device for curing dental composites and diagnosing disease of the oral cavity, comprising:

an enclosure with a light source and delivery optics producing the light necessary for curing dental composites;

a removable optical assembly attached to the distal output end of said delivery optics, wherein said optical assembly comprises a short pass filter, a spacer attached to said short pass filter, and a connection means that fixes said filter with said spacer and said distal output end;

said spacer has a central aperture through which the surface of the oral cavity is illuminated;

said spacer is made of a long pass filter glass that blocks all excitation light incoming through said short pass filter and illuminating the surface of the oral cavity.

6. The device as claimed in claim 5 in which said spacer is from 5 to 20 mm long.

7. The device as claimed in claim 5 in which said aperture is round, and a diameter of said aperture is not smaller than a diameter of the aperture of said delivery optics.

8. The device as claimed in claim 5 in which said aperture is conical with enlarged diameter facing to the surface of the oral cavity and incoming diameter not smaller than a diameter of the aperture of said delivery optics.

9. The device as claimed in claim 5 in which said conical aperture slopes from the axis of said spacer at an angle equals to the output aperture of said delivery optics.

10. The device as claimed in claim 5 in which said short pass filter blocks light having a wavelength more than 470 nm and said spacer transmits light having a wavelength of about 520 nm and more.

11. The device as claimed in claim 5 in which said short pass filter is a band pass filter and blocks all light except that corresponds to maximum absorption of the photosensitizer applied in the oral cavity; said spacer transmits light having a wavelength of about 600 nm and more.

* * * * *